(12) United States Patent
Ding et al.

(10) Patent No.: US 12,338,421 B2
(45) Date of Patent: Jun. 24, 2025

(54) BIOHYDROGEN PRODUCTION DEVICE OF CORN STALKS BASED ON SYNCHRONOUS SACCHARIFICATION AND FERMENTATION AND HYDROGEN PRODUCTION METHOD THEREOF

(71) Applicant: Harbin Institute of Technology, Heilongjiang (CN)

(72) Inventors: Jie Ding, Heilongjiang (CN); Nanqi Ren, Heilongjiang (CN); Bingfeng Liu, Heilongjiang (CN); Shanshan Yang, Heilongjiang (CN)

(73) Assignee: Harbin Institute of Technology, Heilongjiang (CN)

(*) Notice: Subject to any disclaimer, the term of this patent is extended or adjusted under 35 U.S.C. 154(b) by 0 days.

(21) Appl. No.: 18/809,530

(22) Filed: Aug. 20, 2024

(65) Prior Publication Data

US 2025/0145920 A1    May 8, 2025

(30) Foreign Application Priority Data

Nov. 2, 2023    (CN) .......................... 202311448505.X

(51) Int. Cl.
| | | |
|---|---|---|
| *C12M 1/107* | (2006.01) | |
| *C12M 1/00* | (2006.01) | |
| *C12M 1/06* | (2006.01) | |
| *C12M 1/26* | (2006.01) | |

(52) U.S. Cl.
CPC ............ *C12M 21/04* (2013.01); *C12M 23/36* (2013.01); *C12M 23/58* (2013.01); *C12M 27/02* (2013.01); *C12M 31/10* (2013.01); *C12M 33/16* (2013.01); *C12M 45/07* (2013.01)

(58) Field of Classification Search
CPC ...... C12M 21/04; C12M 23/36; C12M 23/58; C12M 27/02
See application file for complete search history.

(56) References Cited

FOREIGN PATENT DOCUMENTS

| | | |
|---|---|---|
| CN | 102191277 A | 9/2011 |
| CN | 102766571 A | 11/2012 |
| CN | 102782116 A | 11/2012 |
| CN | 103923946 A | 7/2014 |
| CN | 105154313 A | 12/2015 |
| CN | 105624026 A | 6/2016 |

(Continued)

OTHER PUBLICATIONS

Machine translation of CN114480080A dated May 13, 2022. (Year: 2022).*

*Primary Examiner* — Elizabeth A Robinson
*Assistant Examiner* — Jonathan E Lepage
(74) *Attorney, Agent, or Firm* — NKL Law; Allen Xue

(57) ABSTRACT

A biohydrogen production device of corn stalks based on synchronous saccharification and fermentation and a hydrogen production method thereof are provided. The biohydrogen production device has a vertical fermenter, an irradiation pretreatment unit, an enzymolysis saccharification unit, a dark fermentation unit, a photofermentation unit, a power supply box and a hydrogen storage tank. The method and device utilize the high specificity of different microorganisms to the substrate to combine the dark fermentation and the process of photofermentation hydrogen production. The method and device can be used for the preparation of hydrogen.

4 Claims, 2 Drawing Sheets

(56) References Cited

FOREIGN PATENT DOCUMENTS

| | | | | |
|---|---|---|---|---|
| CN | 105713926 A | 6/2016 | | |
| CN | 106281976 A | 1/2017 | | |
| CN | 107488578 A | 12/2017 | | |
| CN | 108166293 A | 6/2018 | | |
| CN | 209797970 U | 12/2019 | | |
| CN | 114480080 A | 5/2022 | | |
| CN | 219239635 U | 6/2023 | | |
| CN | 116478798 A | 7/2023 | | |
| CN | 116731828 A | 9/2023 | | |
| JP | 2004121055 A * | 4/2004 | ............ | C12M 21/12 |
| WO | WO-2008073186 A2 * | 6/2008 | ............... | C08B 1/00 |

* cited by examiner

BIOHYDROGEN PRODUCTION DEVICE OF CORN STALKS BASED ON SYNCHRONOUS SACCHARIFICATION AND FERMENTATION AND HYDROGEN PRODUCTION METHOD THEREOF

TECHNICAL FIELD

The present invention belongs to the technical field of bioenergy, and particularly relates to a biohydrogen production device of corn stalks based on synchronous saccharification and fermentation and a hydrogen production method thereof.

BACKGROUND

Hydrogen energy is an ideal clean renewable substitute fuel. Hydrogen energy burns to produce only water and no other greenhouse gases, and can be directly and efficiently converted into electric energy through fuel cells. In many hydrogen production methods, biohydrogen production has multiple advantages such as environmental friendliness, wide range of substrates, simple technology, capability of producing biogas energy with high added value, etc. At the same time, the corn straw is an abundant agricultural waste. Because of sufficient supply and low price, if the corn straw is converted into hydrogen by a microbial technology, not only the cost of hydrogen production can be reduced, but also the waste can be resourced, thereby bringing great social benefits and economic benefits from the perspective of clean energy development and waste utilization.

The process of biohydrogen production can be divided into two categories: photofermentation hydrogen production and hydrogen production by dark fermentation. Wherein the former uses microorganisms of anaerobic photosynthetic bacteria and some algae, and the latter uses anaerobic heterotrophic bacteria. Compared with photosynthetic hydrogen production, the process of hydrogen production by dark fermentation has the advantages of higher hydrogen production rate, no restriction of illumination time, wide range of available organic matter, simple technology, etc., and has more development potential in the research of biohydrogen production from organic waste.

However, the research has shown that besides hydrogen and carbon dioxide, hydrogen production by dark fermentation also produces end metabolites which contain a large amount of low molecular organic acids, and the substrate feedback inhibition of volatile organic acids is the main reason for low quantity and unstable hydrogen production in hydrogen production by dark fermentation. As one of the most ancient bacterial groups, photosynthetic bacteria can form a good microecological hydrogen production system with many organisms, efficiently utilize the volatile organic acids produced by end metabolism of dark fermentation, and further degrade the volatile organic acids into hydrogen and carbon dioxide, thereby effectively solving the feedback inhibition of the organic acids in dark fermentation and making dark fermentation have significant advantages in converting renewable biomass resources to produce hydrogen energy. Therefore, the coupling of photofermentation and dark fermentation not only greatly improves the hydrogen energy conversion efficiency of substrate organic matter, achieves thorough decomposition treatment of substrates and produces high-quality hydrogen, but also reduces the emission of organic waste, reduces the cost of hydrogen production, and achieves the purpose of emission reduction and energy production.

SUMMARY

To solve the problems of poor conversion efficiency of hydrogen energy in substrate organic matter, high emission of organic waste, poor quality of hydrogen production and high cost of hydrogen production in the process of existing hydrogen production by dark fermentation, the present invention provides a biohydrogen production device of corn stalks based on synchronous saccharification and fermentation and a hydrogen production method thereof.

A biohydrogen production device of corn stalks based on synchronous saccharification and fermentation comprises a vertical fermenter, an irradiation pretreatment unit, an enzymolysis saccharification unit, a dark fermentation unit, a photofermentation unit, a power supply box and a hydrogen storage tank; the irradiation pretreatment unit, the enzymolysis saccharification unit, the dark fermentation unit and the power supply box are arranged successively in the vertical fermenter from top to bottom; the irradiation pretreatment unit, the enzymolysis saccharification unit, the dark fermentation unit and the power supply box are fixedly connected with an inner wall of the vertical fermenter; an upper part of a side wall of the vertical fermenter is processed with a feed inlet; the feed inlet is communicated with the irradiation pretreatment unit; a discharge end of the irradiation pretreatment unit is communicated with a feed end of the enzymolysis saccharification unit; an enzyme preparation liquid inlet pipe is inserted in a middle of the side wall of the vertical fermenter; the enzyme preparation liquid inlet pipe is communicated with the enzymolysis saccharification unit; a liquid discharge end of the enzymolysis saccharification unit is communicated with a feed end of the dark fermentation unit; a solid discharge end of the enzymolysis saccharification unit is discharged to the outside of the vertical fermenter through a solid outlet pipe inserted on the side wall of the vertical fermenter and flows into a solid waste tank for unified treatment; a hydrogen-producing bacteria feed pipe is inserted in a lower part of the side wall of the vertical fermenter; the hydrogen-producing bacteria feed pipe is communicated with the dark fermentation unit; a hydrogen production end of the dark fermentation unit is communicated with the hydrogen storage tank; a liquid discharge end of the dark fermentation unit is communicated with a feed end of the photofermentation unit; the photofermentation unit is arranged at an outer side of the vertical fermenter; a hydrogen production end of the photofermentation unit is communicated with the hydrogen storage tank; a discharge end of the photofermentation unit is communicated with a recycling pool; and a power output end of the power supply box is connected with a power input end of the irradiation pretreatment unit, a power input end of the enzymolysis saccharification unit, a power input end of the dark fermentation unit and a power input end of the photofermentation unit respectively through wires.

Further, one strut is arranged respectively at four corners of a bottom of the vertical fermenter; each strut is arranged in a vertical direction; a top of each strut is fixedly connected with the vertical fermenter; and a bottom of each strut is in contact with the ground.

Further, the irradiation pretreatment unit comprises a radiation lighting component, a material conveying mechanism and an anti-radiation isolation plate; the radiation lighting component is fixedly connected to an inner top of the vertical fermenter; the anti-radiation isolation plate is arranged below the radiation lighting component; the anti-radiation isolation plate is fixedly connected with the inner wall of one side of the vertical fermenter; a blanking gap is arranged between the anti-radiation isolation plate and the inner wall of the other side of the vertical fermenter; the material conveying mechanism is fixedly connected to a top of the anti-radiation isolation plate; an irradiation end of the radiation lighting component is arranged towards the material conveying mechanism; a starting end of the material conveying mechanism is arranged directly below the feed inlet; an end of the material conveying mechanism is arranged directly above the blanking gap; and the irradiation pretreatment unit is communicated with the feed end of the enzymolysis saccharification unit through the blanking gap.

Further, the radiation lighting component comprises a lamp tube bracket, a radiation searchlight and a control switch; the lamp tube bracket is fixedly connected to the inner top of the vertical fermenter; the radiation searchlight is installed on the bottom of the lamp tube bracket; the radiation searchlight is arranged towards the material conveying mechanism; the control switch is installed on the lamp tube bracket; the control switch is connected in series with the radiation searchlight and the starting end of the material conveying mechanism through the wires; and a No. 1 power output end in the power supply box is connected with a power input end of the radiation searchlight through the wire.

Further, the material conveying mechanism comprises a material conveyor belt, a bracket, a conveying motor, a driving pulley and a driven pulley; the bracket is fixedly connected to the top of the anti-radiation isolation plate; the driving pulley and the driven pulley are installed on the bracket; the driving pulley and the driven pulley are rotatably connected with the bracket; the conveying motor is arranged at an outer side of the vertical fermenter; a housing of the conveying motor is fixedly connected with an outer side wall of the vertical fermenter; a power output shaft of the conveying motor extends into the vertical fermenter and is connected with a wheel shaft of the driving pulley through a coupling; the power output shaft of the conveying motor is rotatably connected with the side wall of the vertical fermenter through a bearing; the material conveyor belt is sleeved on the driving pulley and the driven pulley; the material conveyor belt is tensioned with the driving pulley and the driven pulley; the starting end of the material conveyor belt is arranged directly below the feed inlet; an end of the material conveyor belt is arranged directly above the blanking gap; and a No. 2 power output end in the power supply box is connected with the power input end of the conveying motor through the wire.

Further, the enzymolysis saccharification unit comprises a solid screw conveyor, a spiral motor, a saccharification liquid outlet pipe, a separation baffle plate and two liquid agitators; the separation baffle plate is arranged below the anti-radiation isolation plate; the solid screw conveyor is installed on the separation baffle plate; the spiral motor is arranged on the outer side of the vertical fermenter; the housing of the spiral motor is fixedly connected with the outer side wall of the vertical fermenter; a power output shaft of the spiral motor extends into the vertical fermenter and is connected with a spiral shaft of the solid screw conveyor through a coupling; the power output shaft of the spiral motor is rotatably connected with the side wall of the vertical fermenter through a bearing; an end of the solid screw conveyor is arranged correspondingly with the solid outlet pipe; a lifting baffle plate is arranged between the end of the solid screw conveyor and the solid outlet pipe; the saccharification liquid outlet pipe is inserted onto the separation baffle plate; the enzymolysis saccharification unit is communicated with the dark fermentation unit through the saccharification liquid outlet pipe; the two liquid agitators are arranged between the solid screw conveyor and the anti-radiation isolation plate; each liquid agitator is correspondingly provided with a stirring motor; each stirring motor is arranged on the outer side of the vertical fermenter; a housing of each stirring motor is fixedly connected with the outer side wall of the vertical fermenter; a power output shaft of the stirring motor extends into the vertical fermenter and is connected with a stirring shaft of the liquid agitator through a coupling; a power output shaft of the stirring motor is rotatably connected with the side wall of the vertical fermenter through a bearing; the enzyme preparation liquid inlet pipe is located above the two liquid agitators; the enzyme preparation liquid inlet pipe is arranged near the bottom of the anti-radiation isolation plate; a No. 3 power output end in the power supply box is connected with a power input end of the spiral motor through a wire; and a No. 4 power output end in the power supply box is connected with power input ends of the two stirring motors through wires.

Further, a discharge end of the saccharification liquid outlet pipe is connected in series with a solenoid valve.

Further, the dark fermentation unit comprises a stirring blade, a transmission motor, a liquid outlet pipe and a No. 1 hydrogen output tube; the stirring blade is arranged below the separation partition plate; the transmission motor is arranged at the outer side of the vertical fermenter; a housing of the transmission motor is fixedly connected with the outer side wall of the vertical fermenter; a power output shaft of the transmission motor extends into the vertical fermenter and is connected with a stirring shaft of the stirring blade through a coupling; a power output shaft of the transmission motor is rotatably connected with the side wall of the vertical fermenter through a bearing; the hydrogen-producing bacteria feed pipe is arranged above a liquid level of enzymolysis saccharification liquid in the dark fermentation unit; a solenoid valve is connected in series on the hydrogen-producing bacteria feed pipe; the liquid outlet pipe is arranged below the liquid level of the enzymolysis saccharification liquid in the dark fermentation unit; a liquid inlet end of the liquid outlet pipe is communicated with the vertical fermenter; a liquid outlet end of the liquid outlet pipe is communicated with the liquid inlet end of the photofermentation unit; the No. 1 hydrogen output tube is arranged above the liquid level of enzymolysis saccharification liquid in the dark fermentation unit; an air inlet end of the No. 1 hydrogen output tube is communicated with the vertical fermenter; an air outlet end of the No. 1 hydrogen output tube is communicated with the hydrogen storage tank; the liquid outlet pipe is connected with a solenoid valve in series; and the No. 1 hydrogen output tube is connected with a No. 1 air delivery valve and a No. 1 check valve in series successively along a gas flow direction.

Further, the photofermentation unit comprises a photoreaction fermentation tank, a outlet pipe, a recirculation pipe, a No. 2 hydrogen output tube and an lighting component; a liquid outlet end of the liquid outlet pipe is communicated with one end of the photoreaction fermentation tank; a No. 1 longitudinal baffle plate group and a No. 2 longitudinal baffle plate group are arranged in the photoreaction fermentation tank; the No. 1 longitudinal baffle plate group comprises a plurality of No. 1 longitudinal baffle plates; the plurality of No. 1 longitudinal baffle plates are successively arranged at an inner bottom of the photoreaction fermentation tank along a length extension direction of the photoreaction fermentation tank; a bottom of each No. 1 longitudinal baffle plate is fixedly connected with the inner bottom of the photoreaction fermentation tank; the No. 2 longitudinal baffle plate group comprises a plurality of No. 2 longitudinal baffle plates; the plurality of No. 2 longitudinal baffle plates are successively arranged at an inner top of the photoreaction fermentation tank along the length extension direction of the photoreaction fermentation tank; a top of each No. 2 longitudinal baffle plate is fixedly connected with the inner top of the photoreaction fermentation tank; each No. 1 longitudinal baffle plate is mispositioned with one No. 2 longitudinal baffle plate; the outlet pipe is communicated with a lower part of the other end of the photoreaction fermentation tank; the recirculation pipe is arranged between the liquid outlet pipe and the outlet pipe; one end of the recirculation pipe is communicated with the liquid outlet pipe; the other end of the recirculation pipe is communicated with the discharge tube; an end of the outlet pipe is connected with a discharging valve in series; the No. 2 hydrogen output tube is arranged on the top of the photoreaction fermentation tank; the No. 2 hydrogen output tube is arranged near the other end of the photoreaction fermentation tank; the air inlet end of the No. 2 hydrogen output tube is communicated with the photoreaction fermentation tank; the air outlet end of the No. 2 hydrogen output tube is communicated with the hydrogen storage tank; the No. 2 hydrogen output tube is connected with a No. 2 air delivery valve and a No. 2 check valve in series successively along the gas flow direction; the top of the photoreaction fermentation tank is sealed through a transparent plate; the lighting component is arranged at an outer top of the photoreaction fermentation tank; a connection part of the lighting component is fixedly connected with an outer top of the photoreaction fermentation tank; and an irradiation end of the lighting component is arranged towards the transparent plate.

A hydrogen production method of the biohydrogen production device of corn stalks based on synchronous saccharification and fermentation is achieved through the following steps:

step 1: firstly, starting the conveying motor through the control switch; adding corn stalk particles to the material conveyor belt from the feed inlet; after the material conveyor belt is covered with corn stalks, controlling the material conveyor belt to stop operating; turning on the radiation searchlight through the control switch for irradiation pretreatment of the corn stalks; and after the irradiation is completed, starting the conveying motor to drop the treated corn stalk particles into the enzymolysis saccharification unit from the material conveyor belt;

step 2: adding a diluted enzyme preparation into the enzymolysis saccharification unit from the enzyme preparation liquid inlet pipe and immersing in the liquid agitator; making the corn stalk particles treated in step 1 enter the enzymolysis saccharification unit and mixing with the diluted enzyme preparation; starting the liquid agitator through a stirring motor to mix materials and the enzyme preparation evenly; fully performing enzymolysis saccharification; intercepting the settled materials by the solid screw conveyor; and pushing the materials to the solid outlet pipe;

step 3: after full enzymolysis saccharification, opening a valve at the discharge end of the saccharification liquid outlet pipe; after the saccharification liquid is exhausted, opening the lifting baffle plate between the solid screw conveyor and the solid outlet pipe; conveying, by the solid screw conveyor, the solid waste to the solid outlet pipe and discharging to the solid waste tank; after the solid waste is exhausted, closing the lifting baffle plate; and operating the material conveyor belt of the irradiation pretreatment unit for dropping the materials after pretreatment into the enzymolysis saccharification unit;

step 4: discharging the enzymolysis liquid obtained after the saccharification treatment in step 3 from the saccharification liquid outlet pipe, and flowing into the dark fermentation unit under the action of gravity; adding a hydrogenogen group from the hydrogen-producing bacteria feed pipe; and opening the stirring blade of the dark fermentation unit to begin hydrogen production by dark fermentation;

step 5: making gas produced by dark fermentation in step 4 pass through an air outlet and come to the hydrogen storage tank along the No. 1 hydrogen output tube; and making liquid containing small molecular acids produced by dark fermentation in step 4 flow through the liquid outlet pipe to the photoreaction fermentation tank for photofermentation hydrogen production;

step 6: an interior of the photoreaction fermentation tank is a curved structure, and a top is provided with an lighting component for illumination; making the liquid containing small molecular acids produced by dark fermentation in step 5 flow through the liquid outlet pipe to the photoreaction fermentation tank for photofermentation hydrogen production; making the materials after photoreaction fermentation flow out of the outlet pipe at a tail of the photoreaction fermentation tank and return to the liquid discharge pipe for recycling; after repeated recycling, opening the discharging valve on the outlet pipe; and making the materials after photoreaction fermentation flow through the outlet pipe to the recycling pool;

step 7: making hydrogen produced by photoreaction fermentation in the photoreaction fermentation tank in step 6 come to the hydrogen storage tank along the No. 2 hydrogen output tube to complete the collection of the hydrogen.

Compared with the prior art, the present application has the following beneficial effects:

1. The biohydrogen production device of corn stalks based on synchronous saccharification and fermentation proposed by the present application uses the high specificity of different microorganisms to the substrate to combine the dark fermentation and the process of photofermentation hydrogen production, which not only greatly improves the hydrogen energy conversion efficiency of substrate organic matter, achieves thorough decomposition treatment of the substrate and produces high-quality hydrogen, but also makes resource utilization of agricultural waste, reduces the cost of hydrogen production, and achieves the purpose of emission reduction and energy production.

2. The biohydrogen production device of corn stalks based on synchronous saccharification and fermentation provided by the present application firstly damages the lignin structure through irradiation pretreatment to ensure the normal progress of the subsequent enzymolysis saccharification reaction, so as to reduce the reaction time and improve the hydrogen production efficiency of the substrate. The hydrogen productivity can be improved through enzymolysis saccharification.

The vertical fermenter saves the floor space and miniaturizes the instrument. The dark fermentation metabolites are used for hydrogen production by fermentation of photosynthetic bacteria. The curved structure cycle of the photoreaction fermentation tank significantly improves the hydrogen production efficiency and fully degrades the organic waste. Hydrogen bioenergy may not cause secondary pollution to the environment, and can replace fossil energy to alleviate the energy crisis.

3. The biohydrogen production device of corn stalks based on synchronous saccharification and fermentation provided by the present application has simple structure, mild reaction conditions and low power consumption. The device adopts batch reaction and is easy to be replaced and controlled. Continuous hydrogen production can be achieved by parallelism of a plurality of devices, thereby ensuring continuous hydrogen production reaction.

BRIEF DESCRIPTIONS OF THE DRAWINGS

In the figures: 1 vertical fermenter; 2 irradiation pretreatment unit; 3 lamp tube bracket; 4 irradiation searchlight; 5 control switch; 6 feed inlet; 7 material conveyor belt; 8 bracket of conveyor belt; 9 anti-radiation baffle plate; 10 enzymolysis saccharification unit; 11 enzyme preparation liquid inlet pipe; 12 liquid agitator; 13 solid screw conveyor; 14 spiral motor; 15 saccharification liquid outlet pipe; 16 solid outlet pipe; 17 hydrogen-producing bacteria feed pipe;

18 dark fermentation unit; 19 separation baffle plate; 20 stirring blade; 21 transmission motor; 22 liquid outlet pipe; 23 No. 1 hydrogen output tube; 24 power supply box; 25 strut; 26 photofermentation unit; 27 photofermentation reaction tank; 28 outlet pipe; 29 recirculation pipe; 30 No. 2 hydrogen output tube; 31 lighting component; 32 hydrogen storage tank; 33 No. 1 longitudinal baffle plate group; and 34 No. 2 longitudinal baffle plate group.

DETAILED DESCRIPTIONS OF EMBODIMENTS

Figure 1:
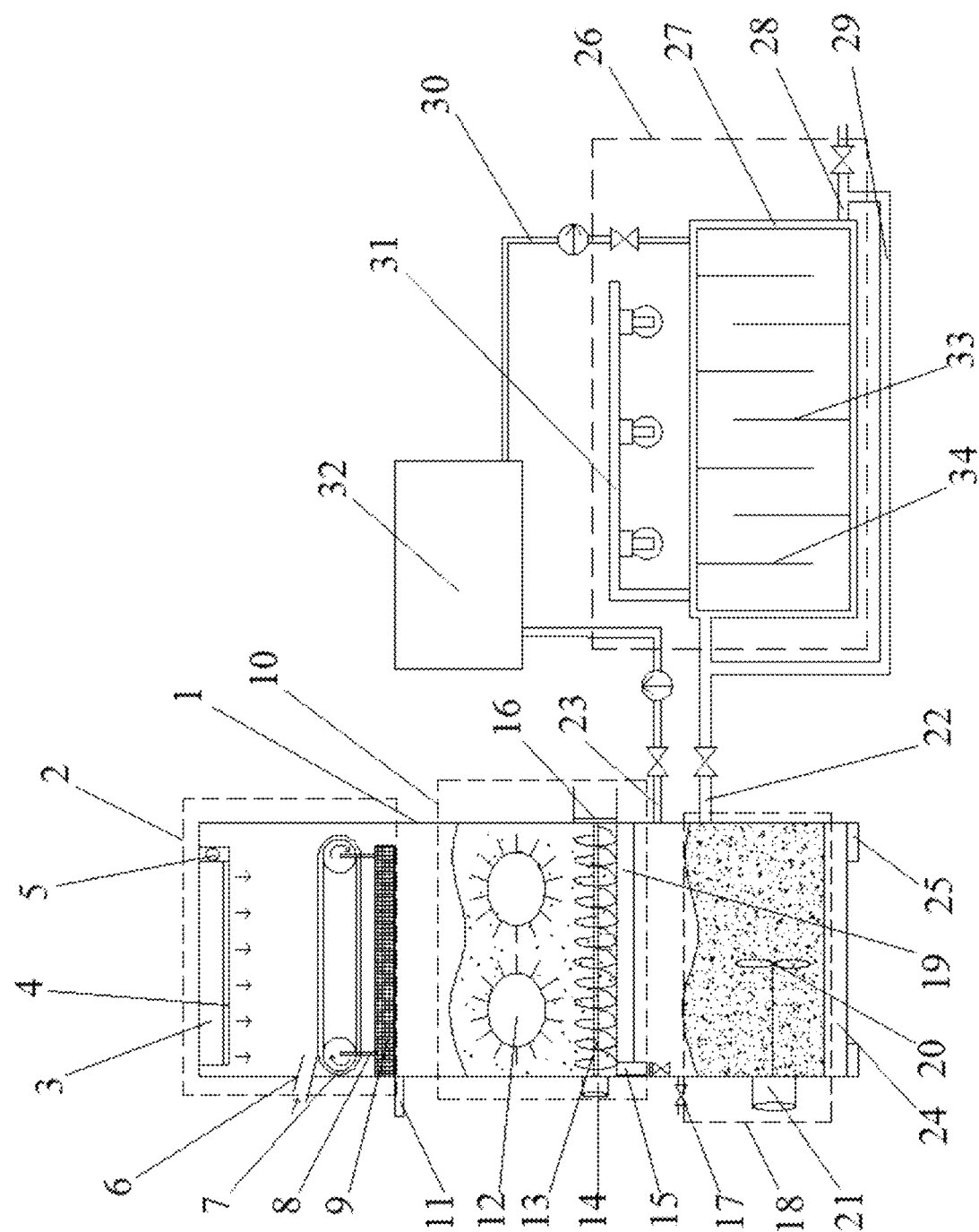
FIG. 1 is a schematic diagram of structural connection of a hydrogen production device in the present application.
Figure 2:
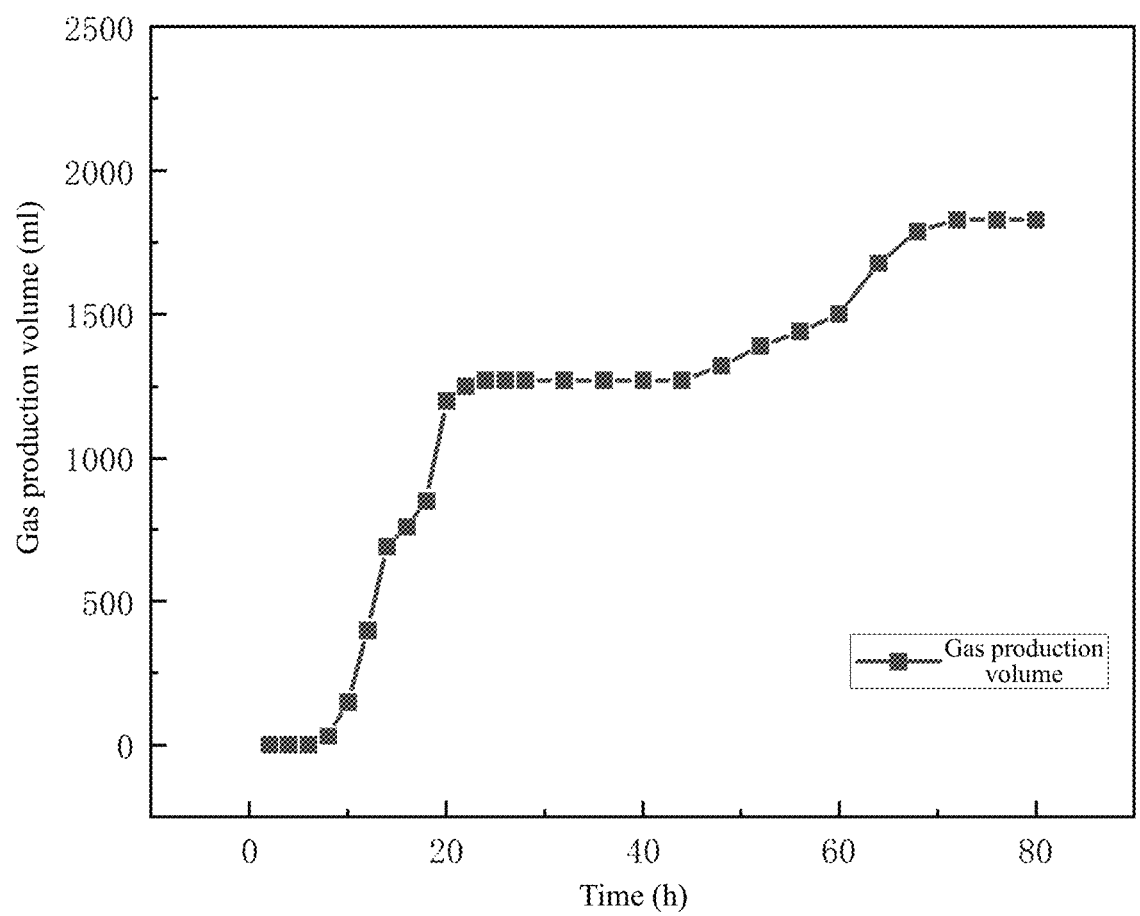
FIG. 2 is an effect diagram of the hydrogen production device and a hydrogen production method of the present application in practical application.

Specific embodiment 1: The present embodiment is illustrated in combination with FIG. 1 to FIG. 2. The embodiment provides a biohydrogen production device of corn stalks based on synchronous saccharification and fermentation. The biohydrogen production device comprises a vertical fermenter 1, an irradiation pretreatment unit 2, an enzymolysis saccharification unit 10, a dark fermentation unit 18, a photofermentation unit 26, a power supply box 24 and a hydrogen storage tank 32. The irradiation pretreatment unit 2, the enzymolysis saccharification unit 10, the dark fermentation unit 18 and the power supply box 24 are arranged successively in the vertical fermenter 1 from top to bottom; the irradiation pretreatment unit 2, the enzymolysis saccharification unit 10, the dark fermentation unit 18 and the power supply box 24 are fixedly connected with an inner wall of the vertical fermenter 1; an upper part of a side wall of the vertical fermenter 1 is processed with a feed inlet 6; the feed inlet 6 is communicated with the irradiation pretreatment unit 2; a discharge end of the irradiation pretreatment unit 2 is communicated with a feed end of the enzymolysis saccharification unit 10; an enzyme preparation liquid inlet pipe 11 is inserted in a middle of the side wall of the vertical fermenter 1; the enzyme preparation liquid inlet pipe 11 is communicated with the enzymolysis saccharification unit 10; a liquid discharge end of the enzymolysis saccharification unit 10 is communicated with a feed end of the dark fermentation unit 18; a solid discharge end of the enzymolysis saccharification unit 10 is discharged to the outside of the vertical fermenter 1 through a solid outlet pipe 16 inserted on the side wall of the vertical fermenter 1 and flows into a solid waste tank for unified treatment; a hydrogen-producing bacteria feed pipe 17 is inserted in a lower part of the side wall of the vertical fermenter 1; the hydrogen-producing bacteria feed pipe 17 is communicated with the dark fermentation unit 18; a hydrogen production end of the dark fermentation unit 18 is communicated with the hydrogen storage tank 32; a liquid discharge end of the dark fermentation unit 18 is communicated with a feed end of the photofermentation unit 26; the photofermentation unit 26 is arranged at an outer side of the vertical fermenter 1; a hydrogen production end of the photofermentation unit 26 is communicated with the hydrogen storage tank 32; a discharge end of the photofermentation unit 26 is communicated with a recycling pool; and a power output end of the power supply box 24 is connected with a power input end of the irradiation pretreatment unit 2, a power input end of the enzymolysis saccharification unit 10, a power input end of the dark fermentation unit 18 and a power input end of the photofermentation unit 26 respectively through wires.

Specific embodiment 2: The present embodiment is illustrated in combination with FIG. 1 to FIG. 2. The differences between the present embodiment and the specific embodiment 1 are that: in the present embodiment, one strut 25 is arranged respectively at four corners of a bottom of the vertical fermenter 1; each strut 25 is arranged in a vertical direction; a top of each strut 25 is fixedly connected with the vertical fermenter 1; and a bottom of each strut 25 is in contact with the ground. Other composition and connection modes are the same as those in specific embodiment 1.

In this arrangement, the vertical fermenter 1 can be supported by the struts 25 to ensure the stability of the vertical fermenter 1.

Specific embodiment 3: The present embodiment is illustrated in combination with FIG. 1 to FIG. 2. The differences between the present embodiment and specific embodiment 2 are that: the irradiation pretreatment unit 2 comprises a radiation lighting component, a material conveying mechanism and an anti-radiation isolation plate 9; the radiation lighting component is fixedly connected to an inner top of the vertical fermenter 1; the anti-radiation isolation plate 9 is arranged below the radiation lighting component; the anti-radiation isolation plate 9 is fixedly connected with the inner wall of one side of the vertical fermenter 1; a blanking gap is arranged between the anti-radiation isolation plate 9 and the inner wall of the other side of the vertical fermenter 1; the material conveying mechanism is fixedly connected to a top of the anti-radiation isolation plate 9; an irradiation end of the radiation lighting component is arranged towards the material conveying mechanism; a starting end of the material conveying mechanism is arranged directly below the feed inlet 6; an end of the material conveying mechanism is arranged directly above the blanking gap; and the irradiation pretreatment unit 2 is communicated with the feed end of the enzymolysis saccharification unit 10 through the blanking gap. Other composition and connection modes are the same as those in specific embodiment 2.

In the present embodiment, the anti-radiation isolation plate 9 is used for separating the irradiation pretreatment unit 22 from the enzymolysis saccharification unit 10, and also isolating the influence of irradiation lamps on the enzymolysis saccharification unit 10 and the dark fermentation unit 18 below the fermenter.

Specific embodiment 4: The present embodiment is illustrated in combination with FIG. 1 to FIG. 2. The differences between the present embodiment and specific embodiment 4 are that: in the present embodiment, the radiation lighting component comprises a lamp tube bracket 3, a radiation searchlight 4 and a control switch 5; the lamp tube bracket 3 is fixedly connected to the inner top of the vertical fermenter 1; the radiation searchlight 4 is installed on the bottom of the lamp tube bracket 3; and the radiation searchlight 4 is arranged towards the material conveying mechanism; the control switch 5 is installed on the lamp tube bracket 3; the control switch 5 is connected in series with the radiation searchlight 4 and the starting end of the material conveying mechanism through the wires; and a No. 1 power output end in the power supply box 24 is connected with a power input end of the radiation searchlight 4 through the wire. Other composition and connection modes are the same as those in specific embodiment 4.

In the present embodiment, the operation and stop of the material conveyor belt 7, the operating speed of the material conveyor belt 7 and the switch of the radiation searchlight 4 can be controlled through the control switch 5. The uniform distribution of the materials on the material conveyor belt 7 enables adequate irradiation pretreatment of the materials to damage the cellulose structure, so as to facilitate subsequent hydrogen production by enzymolysis saccharification.

Specific embodiment 5: The present embodiment is illustrated in combination with FIG. 1 to FIG. 2. The differences between the present embodiment and specific embodiment 4 are that: the material conveying mechanism comprises a material conveyor belt 7, a bracket 8, a conveying motor, a driving pulley and a driven pulley; the bracket 8 is fixedly connected to the top of the anti-radiation isolation plate 9; the driving pulley and the driven pulley are installed on the bracket 8; the driving pulley and the driven pulley are rotatably connected with the bracket 8; the conveying motor is arranged at an outer side of the vertical fermenter 1; a housing of the conveying motor is fixedly connected with an outer side wall of the vertical fermenter 1; a power output shaft of the conveying motor extends into the vertical fermenter 1 and is connected with a wheel shaft of the driving pulley through a coupling; the power output shaft of the conveying motor is rotatably connected with the side wall of the vertical fermenter 1 through a bearing; the material conveyor belt 7 is sleeved on the driving pulley and the driven pulley; the material conveyor belt 7 is tensioned with the driving pulley and the driven pulley; the starting end of the material conveyor belt 7 is arranged directly below the feed inlet 6; an end of the material conveyor belt 7 is arranged directly above the blanking gap; and a No. 2 power output end in the power supply box 24 is connected with the power input end of the conveying motor through the wire. Other composition and connection modes are the same as those in specific embodiment 4.

Specific embodiment 6: The present embodiment is illustrated in combination with FIG. 1 to FIG. 2. The differences between the present embodiment and specific embodiment 5 are that: in the present embodiment, the enzymolysis saccharification unit 10 comprises a solid screw conveyor 13, a spiral motor 14, a saccharification liquid outlet pipe 15, a separation baffle plate 19 and two liquid agitators 12; the separation baffle plate 19 is arranged below the anti-radiation isolation plate 9; the solid screw conveyor 13 is installed on the separation baffle plate 19; the spiral motor 14 is arranged on the outer side of the vertical fermenter 1; the housing of the spiral motor 14 is fixedly connected with the outer side wall of the vertical fermenter 1; a power output shaft of the spiral motor 14 extends into the vertical fermenter 1 and is connected with a spiral shaft of the solid screw conveyor 13 through a coupling; the power output shaft of the spiral motor 14 is rotatably connected with the side wall of the vertical fermenter 1 through a bearing; an end of the solid screw conveyor 13 is arranged correspondingly with the solid outlet pipe 16; a lifting baffle plate is arranged between the end of the solid screw conveyor 13 and the solid outlet pipe 16; the saccharification liquid outlet pipe 15 is inserted onto the separation baffle plate 19; the enzymolysis saccharification unit 10 is communicated with the dark fermentation unit 18 through the saccharification liquid outlet pipe 15; the two liquid agitators 12 are arranged between the solid screw conveyor 13 and the anti-radiation isolation plate 9; each liquid agitator 12 is correspondingly provided with a stirring motor; each stirring motor is arranged on the outer side of the vertical fermenter 1; a housing of each stirring motor is fixedly connected with the outer side wall of the vertical fermenter 1; a power output shaft of the stirring motor extends into the vertical fermenter 1 and is connected with a stirring shaft of the liquid agitator 12 through a coupling; a power output shaft of the stirring motor is rotatably connected with the side wall of the vertical fermenter 1 through a bearing; the enzyme preparation liquid inlet pipe 11 is located above the two liquid agitators 12; the enzyme preparation liquid inlet pipe 11 is arranged near the bottom of the anti-radiation isolation plate 9; a No. 3 power output end in the power supply box 24 is connected with a power input end of the spiral motor 14 through a wire; and a No. 4 power output end in the power supply box 24 is connected with power input ends of the two stirring motors through wires. Other composition and connection modes are the same as those in specific embodiment 5.

Specific embodiment 7: The present embodiment is illustrated in combination with FIG. 1 to FIG. 2. The differences between the present embodiment and specific embodiment 6 are that: in the present embodiment, a discharge end of the saccharification liquid outlet pipe 15 is connected in series with a solenoid valve. Other composition and connection modes are the same as those in specific embodiment 6.

Specific embodiment 8: The present embodiment is illustrated in combination with FIG. 1 to FIG. 2. The differences between the present embodiment and specific embodiment 7 are that: in the present embodiment, the dark fermentation unit 18 comprises a stirring blade 20, a transmission motor 21, a liquid outlet pipe 22 and a No. 1 hydrogen output tube 23; the stirring blade 20 is arranged below the separation partition plate 19; the transmission motor 21 is arranged at the outer side of the vertical fermenter 1; a housing of the transmission motor 21 is fixedly connected with the outer side wall of the vertical fermenter 1; a power output shaft of the transmission motor 21 extends into the vertical fermenter 1 and is connected with a stirring shaft of the stirring blade 20 through a coupling; a power output shaft of the transmission motor 21 is rotatably connected with the side wall of the vertical fermenter 1 through a bearing; the hydrogen-producing bacteria feed pipe 17 is arranged above a liquid level of enzymolysis saccharification liquid in the dark fermentation unit 18; a solenoid valve is connected in series on the hydrogen-producing bacteria feed pipe 17; the liquid outlet pipe 22 is arranged below the liquid level of the enzymolysis saccharification liquid in the dark fermentation unit 18; a liquid inlet end of the liquid outlet pipe 22 is communicated with the vertical fermenter 1; a liquid outlet end of the liquid outlet pipe 22 is communicated with the liquid inlet end of the photofermentation unit 26; the No. 1 hydrogen output tube 23 is arranged above the liquid level of enzymolysis saccharification liquid in the dark fermentation unit 18; an air inlet end of the No. 1 hydrogen output tube 23 is communicated with the vertical fermenter 1; an air outlet end of the No. 1 hydrogen output tube 23 is communicated with the hydrogen storage tank 32; the liquid outlet pipe 22 is connected with a solenoid valve in series; and the No. 1 hydrogen output tube 23 is connected with a No. 1 air delivery valve and a No. 1 check valve in series successively along a gas flow direction. Other composition and connection modes are the same as those in specific embodiment 7.

In the present embodiment, the stirring blade 20 and the transmission motor 21 are arranged in a dark fermentation reaction component. The product after enzymolysis is fully stirred and mixed with the material in the dark fermentation unit 18 through the stirring blade 20 to ensure the stability and continuity of the hydrogen production process. The produced hydrogen enters the hydrogen storage tank 36 through the No. 1 hydrogen output tube 23. The liquid containing small molecular acids produced by dark fermentation enters the photoreaction fermentation tank 27 through a liquid discharge port for subsequent photoreaction hydrogen production work.

Specific embodiment 9: The present embodiment is illustrated in combination with FIG. 1 to FIG. 2. The differences between the present embodiment and specific embodiment 8 are that: in the present embodiment, the photofermentation unit 26 comprises a photoreaction fermentation tank 27, an outlet pipe 28, a recirculation pipe 29, a No. 2 hydrogen output tube 30 and an lighting component 31; a liquid outlet end of the liquid outlet pipe 22 is communicated with one end of the photoreaction fermentation tank 27; a No. 1 longitudinal baffle plate group 33 and a No. 2 longitudinal baffle plate group 34 are arranged in the photoreaction fermentation tank 27; the No. 1 longitudinal baffle plate group 33 comprises a plurality of No. 1 longitudinal baffle plates; the plurality of No. 1 longitudinal baffle plates are successively arranged at an inner bottom of the photoreaction fermentation tank 27 along a length extension direction of the photoreaction fermentation tank 27; a bottom of each No. 1 longitudinal baffle plate is fixedly connected with the inner bottom of the photoreaction fermentation tank 27; the No. 2 longitudinal baffle plate group 34 comprises a plurality of No. 2 longitudinal baffle plates; the plurality of No. 2 longitudinal baffle plates are successively arranged at an inner top of the photoreaction fermentation tank 27 along the length extension direction of the photoreaction fermentation tank 27; a top of each No. 2 longitudinal baffle plate is fixedly connected with the inner top of the photoreaction fermentation tank 27; each No. 1 longitudinal baffle plate is mispositioned with one No. 2 longitudinal baffle plate; the outlet pipe 28 is communicated with a lower part of the other end of the photoreaction fermentation tank 27; the recirculation pipe 29 is arranged between the liquid outlet pipe 22 and the outlet pipe 28; one end of the recirculation pipe 29 is communicated with the liquid outlet pipe 22; the other end of the recirculation pipe 29 is communicated with the discharge tube 28; an end of the outlet pipe 28 is connected with a discharging valve in series; the No. 2 hydrogen output tube 30 is arranged on the top of the photoreaction fermentation tank 27; the No. 2 hydrogen output tube 30 is arranged near the other end of the photoreaction fermentation tank 27; the air inlet end of the No. 2 hydrogen output tube 30 is communicated with the photoreaction fermentation tank 27; the air outlet end of the No. 2 hydrogen output tube 30 is communicated with the hydrogen storage tank 32; the No. 2 hydrogen output tube 30 is connected with a No. 2 air delivery valve and a No. 2 check valve in series successively along the gas flow direction; the top of the photoreaction fermentation tank 27 is sealed through a transparent plate; the lighting component 31 is arranged at an outer top of the photoreaction fermentation tank 27; a connection part of the lighting component 31 is fixedly connected with an outer top of the photoreaction fermentation tank 27; and an irradiation end of the lighting component 31 is arranged towards the transparent plate. Other composition and connection modes are the same as those in specific embodiment 8.

In the present embodiment, through the arrangement of the No. 1 longitudinal baffle plate group 34 and the No. 2 longitudinal baffle plate group 35, a curved path is formed inside the photoreaction fermentation tank 27. The cycle of the curved structure path can significantly increase the hydrogen production efficiency and facilitate the full degradation of the organic waste. To stabilize the photoreaction, the lighting component 31 comprises a lifting longitudinal adjustment structure and a double-light source illumination head. The lifting longitudinal structure is an electrically driven lead screw nut structure. The double-light source illumination head is installed on the lead screw nut through a fixing seat, and rotates by a motor located at the top of the longitudinal structure to drive the lead screw to rotate and also drive a nut located on a lead screw to move along the axis extension direction of the lead screw. The double-light source illumination head is driven by the movement of the nut to achieve the lifting effect. The distance between the double-light source illumination head and the photoreaction fermentation tank 27 is adjusted to indirectly adjust the intensity and irradiation area of the illumination, so that the material in the photoreaction fermentation tank 27 can react more fully. The double-light source illumination head comprises two lamp sources. One lamp source is an LED lamp, and the other lamp source is a yellow-light lamp. The light source of illumination during work can be selected according to the photoreaction characteristics of the material to make the photoreaction more stable. The recirculation pipe 29 considers that the material in the photoreaction fermentation tank 27 performs a motion reaction along the curved path in the photoreaction fermentation tank 27 and the reaction is not complete. Therefore, in order to make the material react more fully, the microbial inoculum after photoreaction is recycled through the recirculation pipe 29 and reused repeatedly to produce hydrogen, so as to achieve the purpose of making full use of the hydrogenogen group.

Specific embodiment 10: The present embodiment is illustrated in combination with FIG. 1 to FIG. 2. The present embodiment proposes a hydrogen production method of the biohydrogen production device of corn stalks based on synchronous saccharification and fermentation. The method is achieved through the following steps:

step 1: firstly, starting the conveying motor through the control switch 5; adding corn stalk particles to the material conveyor belt 7 from the feed inlet 6; after the material conveyor belt 7 is covered with corn stalks, controlling the material conveyor belt 7 to stop operating; turning on the radiation searchlight 4 through the control switch 5 for irradiation pretreatment of the corn stalks; and after the irradiation is completed, starting the conveying motor to drop the treated corn stalk particles into the enzymolysis saccharification unit 10 from the material conveyor belt 7;

step 2: adding a diluted enzyme preparation into the enzymolysis saccharification unit 10 from the enzyme preparation liquid inlet pipe 11 and immersing in the liquid agitator 12; making the corn stalk particles treated in step 1 enter the enzymolysis saccharification unit 10 and mixing with the diluted enzyme preparation; starting the liquid agitator through a stirring motor to mix materials and the enzyme preparation evenly; fully performing enzymolysis saccharification; intercepting the settled materials by the solid screw conveyor 13; and pushing the materials to the solid outlet pipe 16;

step 3: after full enzymolysis saccharification, opening a valve at the discharge end of the saccharification liquid outlet pipe 15; after the saccharification liquid is exhausted, opening the lifting baffle plate between the solid screw conveyor 13 and the solid outlet pipe 16; conveying, by the solid screw conveyor 13, the solid waste to the solid outlet pipe 16 and discharging to the solid waste tank; after the solid waste is exhausted, closing the lifting baffle plate; and operating the material conveyor belt 7 of the irradiation pretreatment unit 2 for dropping the materials after pretreatment into the enzymolysis saccharification unit 10;

step 4: discharging the enzymolysis liquid obtained after the saccharification treatment in step 3 from the saccharification liquid outlet pipe 15, and flowing into the dark fermentation unit 18 under the action of gravity; adding a hydrogenogen group from the hydrogen-producing bacteria feed pipe 17; and opening the stirring blade 20 of the dark fermentation unit 18 to begin hydrogen production by dark fermentation;

step 5: making gas produced by dark fermentation in step 4 pass through an air outlet and come to the hydrogen storage tank 32 along the No. 1 hydrogen output tube 23; and making liquid containing small molecular acids produced by dark fermentation in step 4 flow through the liquid outlet pipe 22 to the photoreaction fermentation tank 27 for photofermentation hydrogen production;

step 6: an interior of the photoreaction fermentation tank 27 is a curved structure, and a top is provided with an lighting component 31 for illumination; making the liquid containing small molecular acids produced by dark fermentation in step 5 flow through the liquid outlet pipe 22 to the photoreaction fermentation tank 27 for photofermentation hydrogen production; making the materials after photoreaction fermentation flow out of the outlet pipe 28 at a tail of the photoreaction fermentation tank 27 and return to the liquid discharge pipe 22 for recycling; after repeated recycling, opening the discharging valve on the outlet pipe 28; and making the materials after photoreaction fermentation flow through the outlet pipe to the recycling pool;

step 7: making hydrogen produced by photoreaction fermentation in the photoreaction fermentation tank 27 in step 6 come to the hydrogen storage tank 32 along the No. 2 hydrogen output tube 30 to complete the collection of the hydrogen.

In the present embodiment, in step 1, the corn stalks are irradiated with 800 kGy for 48 h. In step 2, cellulase is added at an enzyme load of 150 mg/g, and the pre-treated material is hydrolyzed for at 55° C. for 48 h. 0.05 mol/L sodium citrate solution is used as a buffer solution. In step 4, dark fermentation hydrogenogen is inoculated into the saccharification liquid product according to the inoculation amount with a mass ratio of 15-25%. The controlled temperature of photofermentation hydrogen production is 30-40° C., and the pH is 6.5-7.0. Liquid phase metabolites enter the photoreaction fermentation tank after dark reaction hydrogen production in step 5. The photofermentation hydrogenogen is inoculated into the liquid phase product produced in the dark fermentation process according to the inoculation amount with a mass ratio of 10-15%. The controlled temperature of photofermentation hydrogen production is 30-45° C., and the pH is 7.0-8.0. The light source is yellow light. Photofermentation hydrogen production is carried out under the illumination intensity of 2500-5500 lux. In the steps of dark fermentation hydrogen production in step 4 and photofermentation hydrogen production in steps 5-7, the gas production volume needs to be measured by a gas flowmeter and the hydrogen storage tank device is used for collection. The produced hydrogen can be purified at first, and dry and pure hydrogen can be obtained through a sodium hydroxide solution, an anhydrous magnesium sulfate desiccant and a hydrogen compressor, and stored into the hydrogen tank.

The present invention is disclosed above through preferred embodiments. However, the above preferred embodiments are not used to limit the present invention. Any of those skilled in the art may make some amendments or modifications to the above disclosed structure and technical content into equivalent embodiments with equivalent change without departing from the scope of the technical solution of the present invention. However, any simple amendment, equivalent change and modification made to the above embodiments according to the technical essence of the present invention without departing from the content of the technical solution of the present invention shall still belong to the scope of the technical solution of the present invention.

What is claimed is:

1. A biohydrogen production device, comprising an irradiation pretreatment unit (2), an enzymolysis saccharification unit (10), a dark fermentation unit (18), a photofermentation unit (26), a power supply box (24) and a hydrogen storage tank (32) successively arranged in a vertical fermenter (1) from top to bottom,
wherein:
the irradiation pretreatment unit (2), the enzymolysis saccharification unit (10), the dark fermentation unit (18) and the power supply box (24) are fixedly connected with an inner wall of the vertical fermenter (1);
an upper part of a side wall of the vertical fermenter (1) is provided with a feed inlet (6);
the feed inlet (6) is in communication with the irradiation pretreatment unit (2);
a discharge end of the irradiation pretreatment unit (2) is in communication with a feed end of the enzymolysis saccharification unit (10);
an enzyme preparation liquid inlet pipe (11) is disposed in a middle of the side wall of the vertical fermenter (1);
the enzyme preparation liquid inlet pipe (11) is in communication with the enzymolysis saccharification unit (10);
a liquid discharge end of the enzymolysis saccharification unit (10) is in communication with a feed end of the dark fermentation unit (18);
a solid discharge end of the enzymolysis saccharification unit (10) is discharged through a solid outlet pipe (16) into a solid waste tank;
a hydrogen-producing bacteria feed pipe (17) is inserted in a lower part of the side wall of the vertical fermenter (1) and in communication with the dark fermentation unit (18);
a hydrogen production end of the dark fermentation unit (18) is in communication with the hydrogen storage tank (32);
a liquid discharge end of the dark fermentation unit (18) is in communication with a feed end of the photofermentation unit (26);
the photofermentation unit (26) is arranged outside of the vertical fermenter (1);
a hydrogen production end of the photofermentation unit (26) is in communication with the hydrogen storage tank (32);
a discharge end of the photofermentation unit (26) is in communication with a recycling pool; and
a power output end of the power supply box (24) is connected with the irradiation pretreatment unit (2), the enzymolysis saccharification unit (10), the dark fermentation unit (18), and the photofermentation unit (26) respectively-through wires;
the irradiation pretreatment unit (2) comprises:
a radiation lighting component, a material conveying mechanism, and an anti-radiation isolation plate (9), wherein:
the radiation lighting component is fixedly connected to an inner top of the vertical fermenter (1);
the anti-radiation isolation plate (9) is arranged below the radiation lighting component and fixedly connected with the inner wall of one side of the vertical fermenter (1);
a blanking gap is arranged between the anti-radiation isolation plate (9) and the inner wall of the other side of the vertical fermenter (1);
the material conveying mechanism is fixedly connected to a top of the anti-radiation isolation plate (9);
an irradiation end of the radiation lighting component is arranged towards the material conveying mechanism;
a starting end of the material conveying mechanism is arranged directly below the feed inlet (6);
an end of the material conveying mechanism is arranged directly above the blanking gap; and
the irradiation pretreatment unit (2) is communicated with the feed end of the enzymolysis saccharification unit (10) through the blanking gap;
the radiation lighting component comprises a lamp tube bracket (3), a radiation searchlight (4) and a control switch (5), wherein:
the lamp tube bracket (3) is fixedly connected to the inner top of the vertical fermenter (1);
the radiation searchlight (4) is installed on the bottom of the lamp tube bracket (3);
the radiation searchlight (4) is arranged towards the material conveying mechanism;
the control switch (5) is installed on the lamp tube bracket (3);
the control switch (5) is connected in series with the radiation searchlight (4) and the starting end of the material conveying mechanism; and
a first power output end in the power supply box (24) is connected with a power input end of the radiation searchlight (4);
the material conveying mechanism comprises a material conveyor belt (7), a bracket (8), a conveying motor, a driving pulley and a driven pulley, wherein:
the bracket (8) is fixedly connected to the top of the anti-radiation isolation plate (9);
the driving pulley and the driven pulley are installed on the bracket (8);
the driving pulley and the driven pulley are rotatably connected with the bracket (8);
the conveying motor is arranged at an outer side of the vertical fermenter (1);
a housing of the conveying motor is fixedly connected with an outer side wall of the vertical fermenter (1);
a power output shaft of the conveying motor extends into the vertical fermenter (1) and is connected with a wheel shaft of the driving pulley through a coupling;
the power output shaft of the conveying motor is rotatably connected with the side wall of the vertical fermenter (1) through a bearing;
the material conveyor belt (7) is sleeved on the driving pulley and the driven pulley and is tensioned with the driving pulley and the driven pulley;
the starting end of the material conveyor belt (7) is arranged directly below the feed inlet (6);
an end of the material conveyor belt (7) is arranged directly above the blanking gap; and a second power output end in the power supply box (24) is connected with the power input end of the conveying motor:
wherein the enzymolysis saccharification unit (10) comprises a solid screw conveyor (13), a spiral motor (14), a saccharification liquid outlet pipe (15), a separation baffle plate (19) and two liquid agitators (12), wherein:
the separation baffle plate (19) is arranged below the anti-radiation isolation plate (9);
the solid screw conveyor (13) is installed on the separation baffle plate (19);
the spiral motor (14) is arranged on the outer side of the vertical fermenter (1);

the housing of the spiral motor (14) is fixedly connected with the outer side wall of the vertical fermenter (1);
a power output shaft of the spiral motor (14) extends into the vertical fermenter (1) and is connected with a spiral shaft of the solid screw conveyor (13) through a coupling;
the power output shaft of the spiral motor (14) is rotatably connected with the side wall of the vertical fermenter (1) through a bearing;
an end of the solid screw conveyor (13) is arranged correspondingly with the solid outlet pipe (16);
a lifting baffle plate is arranged between the end of the solid screw conveyor (13) and the solid outlet pipe (16);
the saccharification liquid outlet pipe (15) is inserted onto the separation baffle plate (19);
the enzymolysis saccharification unit (10) is communicated with the dark fermentation unit (18) through the saccharification liquid outlet pipe (15);
the two liquid agitators (12) are arranged between the solid screw conveyor (13) and the anti-radiation isolation plate (9);
each liquid agitator (12) is correspondingly provided with a stirring motor; each stirring motor is arranged on the outer side of the vertical fermenter (1);
a housing of each stirring motor is fixedly connected with the outer side wall of the vertical fermenter (1);
a power output shaft of the stirring motor extends into the vertical fermenter (1) and is connected with a stirring shaft of the liquid agitator (12) through a coupling; a power output shaft of the stirring motor is rotatably connected with the side wall of the vertical fermenter (1) through a bearing;
the enzyme preparation liquid inlet pipe (11) is located above the two liquid agitators (12); a third power output end in the power supply box (24) is connected with a power input end of the spiral motor (14); and
a fourth power output end in the power supply box (24) is connected with power input ends of the two stirring motors:
wherein the dark fermentation unit (18) comprises a stirring blade (20), a transmission motor (21), a liquid outlet pipe (22) and a first hydrogen output tube (23), wherein:
the stirring blade (20) is arranged below the separation partition plate (19);
the transmission motor (21) is arranged at the outer side of the vertical fermenter (1);
a housing of the transmission motor (21) is fixedly connected with the outer side wall of the vertical fermenter (1);
a power output shaft of the transmission motor (21) extends into the vertical fermenter (1) and is connected with a stirring shaft of the stirring blade (20) through a coupling;
a power output shaft of the transmission motor (21) is rotatably connected with the side wall of the vertical fermenter (1) through a bearing; the hydrogen-producing bacteria feed pipe (17) is arranged above a liquid level of enzymolysis saccharification liquid in the dark fermentation unit (18);
a solenoid valve is connected in series on the hydrogen-producing bacteria feed pipe (17);
the liquid outlet pipe (22) is arranged below the liquid level of the enzymolysis saccharification liquid in the dark fermentation unit (18);
a liquid inlet end of the liquid outlet pipe (22) is communicated with the vertical fermenter (1);
a liquid outlet end of the liquid outlet pipe (22) is communicated with the liquid inlet end of the photofermentation unit (26);
the first hydrogen output tube (23) is arranged above the liquid level of enzymolysis saccharification liquid in the dark fermentation unit (18);
an air inlet end of the first hydrogen output tube (23) is in communication with the vertical fermenter (1);
an air outlet end of the first hydrogen output tube (23) is in communication with the hydrogen storage tank (32);
the liquid outlet pipe (22) is connected with a solenoid valve in series; and
the first hydrogen output tube (23) is connected with a first air delivery valve and a first check valve in series successively along a gas flow direction:
the photofermentation unit (26) comprises a photoreaction fermentation tank (27), a outlet pipe (28), a recirculation pipe (29), second hydrogen output tube (30) and an lighting component (31), wherein:
a liquid outlet end of the liquid outlet pipe (22) is in communication with one end of the photoreaction fermentation tank (27);
a first longitudinal baffle plate group (33) and second longitudinal baffle plate group (34) are arranged in the photoreaction fermentation tank (27);
the first longitudinal baffle plate group (33) comprises a plurality of first longitudinal baffle plates;
the plurality of first longitudinal baffle plates are successively arranged at an inner bottom of the photoreaction fermentation tank (27) along a length extension direction of the photoreaction fermentation tank (27);
a bottom of each first longitudinal baffle plate is fixedly connected with the inner bottom of the photoreaction fermentation tank (27);
the second longitudinal baffle plate group (34) comprises a plurality of second longitudinal baffle plates;
the plurality of second longitudinal baffle plates are successively arranged at an inner top of the photoreaction fermentation tank (27) along the length extension direction of the photoreaction fermentation tank (27);
a top of each second longitudinal baffle plate is fixedly connected with the inner top of the photoreaction fermentation tank (27);
each first longitudinal baffle plate is mispositioned with one second longitudinal baffle plate;
the outlet pipe (28) is in communication with a lower part of the other end of the photoreaction fermentation tank (27);
the recirculation pipe (29) is arranged between the liquid outlet pipe (22) and the outlet pipe (28);
a first end of the recirculation pipe (29) is in communication with the liquid outlet pipe (22) and a second; the other end of the recirculation pipe (29) is communicated with the discharge tube (28);
an end of the outlet pipe (28) is connected with a discharging valve in series;
the second hydrogen output tube (30) is arranged on the top of the photoreaction fermentation tank (27);
the second hydrogen output tube (30) is arranged near the other end of the photoreaction fermentation tank (27);

the air inlet end of the second hydrogen output tube (30) is in communication with the photoreaction fermentation tank (27);

the air outlet end of the second hydrogen output tube (30) is in communication with the hydrogen storage tank (32);

the second hydrogen output tube (30) is connected with a second air delivery valve and a second check valve in series successively along the gas flow direction;

the top of the photoreaction fermentation tank (27) is sealed through a transparent plate;

the lighting component (31) is arranged at an outer top of the photoreaction fermentation tank (27);

a connection part of the lighting component (31) is fixedly connected with an outer top of the photoreaction fermentation tank (27); and an irradiation end of the lighting component (31) is arranged towards the transparent plate;

the lighting component (31) comprises a lifting longitudinal adjustment structure and a double-light source illumination head, wherein:

the lifting longitudinal structure is an electrically driven lead screw nut structure:

the double-light source illumination head is installed on the lead screw nut through a fixing seat, and configured to be rotated by a motor located at the top of the longitudinal structure to drive the lead screw to rotate and also drive a nut located on a lead screw to move along the axis extension direction of the lead screw:

the double-light source illumination head is configured to be driven by the movement of the nut to achieve the lifting effect:

a distance between the double-light source illumination head and the photoreaction fermentation tank (27) is adjustable to indirectly adjust the intensity and irradiation area of the illumination;

wherein the double-light source illumination head comprises an LED lamp, and a yellow-light lamp.

2. The biohydrogen production device according to claim 1, wherein one strut (25) is arranged respectively at four corners of a bottom of the vertical fermenter (1); each strut (25) is arranged in a vertical direction; a top of each strut (25) is fixedly connected with the vertical fermenter (1); and a bottom of each strut (25) is in contact with the ground.

3. The biohydrogen production device according to claim 2, wherein a discharge end of the saccharification liquid outlet pipe (15) is connected in series with a solenoid valve.

4. A hydrogen production method using the biohydrogen production device according to claim 1, comprising:

step 1: firstly, starting the conveying motor through the control switch (5); adding corn stalk particles to the material conveyor belt (7) from the feed inlet (6); after the material conveyor belt (7) is covered with corn stalks, controlling the material conveyor belt (7) to stop operating; turning on the radiation searchlight (4) through the control switch (5) for irradiation pretreatment of the corn stalks; and after the irradiation is completed, starting the conveying motor to drop the treated corn stalk particles into the enzymolysis saccharification unit (10) from the material conveyor belt (7);

step 2: adding a diluted enzyme preparation into the enzymolysis saccharification unit (10) from the enzyme preparation liquid inlet pipe (11) and immersing in the liquid agitator (12); making the corn stalk particles treated in step 1 enter the enzymolysis saccharification unit (10) and mixing with the diluted enzyme preparation; starting the liquid agitator through a stirring motor to mix materials and the enzyme preparation evenly; fully performing enzymolysis saccharification; intercepting the settled materials by the solid screw conveyor (13); and pushing the materials to the solid outlet pipe (16);

step 3: after full enzymolysis saccharification, opening a valve at the discharge end of the saccharification liquid outlet pipe (15); after the saccharification liquid is exhausted, opening the lifting baffle plate between the solid screw conveyor (13) and the solid outlet pipe (16); conveying, by the solid screw conveyor (13), the solid waste to the solid outlet pipe (16) and discharging to the solid waste tank; after the solid waste is exhausted, closing the lifting baffle plate; and operating the material conveyor belt (7) of the irradiation pretreatment unit (2) for dropping the materials after pretreatment into the enzymolysis saccharification unit (10);

step 4: discharging the enzymolysis liquid obtained after the saccharification treatment in step 3 from the saccharification liquid outlet pipe (15), and flowing into the dark fermentation unit (18) under the action of gravity; adding a hydrogenogen group from the hydrogen-producing bacteria feed pipe (17); and opening the stirring blade (20) of the dark fermentation unit (18) to begin hydrogen production by dark fermentation;

step 5: passing a gas produced by dark fermentation in step 4 through an air outlet and come to the hydrogen storage tank (32) along the First hydrogen output tube (23); and passing a liquid containing small molecular acids produced by dark fermentation in step 4 through the liquid outlet pipe (22) to the photoreaction fermentation tank (27) for photofermentation hydrogen production;

step 6: wherein an interior of the photoreaction fermentation tank (27) has a curved structure, and a top is provided with an lighting component (31) for illumination; making the liquid containing small molecular acids produced by dark fermentation in step 5 flow through the liquid outlet pipe (22) to the photoreaction fermentation tank (27) for photofermentation hydrogen production; making the materials after photoreaction fermentation flow out of the outlet pipe (28) at a tail of the photoreaction fermentation tank (27) and returning to the liquid discharge pipe (22) for recycling; after repeated recycling, opening the discharging valve on the outlet pipe (28); and making the materials after photoreaction fermentation flow through the outlet pipe to the recycling pool; and step 7: feeding hydrogen produced by photoreaction fermentation in the photoreaction fermentation tank (27) in step 6 to the hydrogen storage tank (32) along the second hydrogen output tube (30) to complete the collection of the hydrogen.

* * * * *